(12) United States Patent
Cheng et al.

(10) Patent No.: US 11,389,637 B2
(45) Date of Patent: Jul. 19, 2022

(54) SYSTEMS AND METHODS FOR DIRECTING FLUID FLOW

(71) Applicant: Human Hydrology Devices, Houston, TX (US)

(72) Inventors: Jed-Sian Cheng, Houston, TX (US); Mostafa Jubayar Hasan, Houston, TX (US)

(73) Assignee: HUMAN HYDROLOGY DEVICES, Houston, TX (US)

( * ) Notice: Subject to any disclaimer, the term of this patent is extended or adjusted under 35 U.S.C. 154(b) by 0 days.

(21) Appl. No.: 17/364,324

(22) Filed: Jun. 30, 2021

(65) Prior Publication Data

US 2021/0322754 A1    Oct. 21, 2021

(51) Int. Cl.
*A61M 39/22*    (2006.01)
*A61M 39/10*    (2006.01)

(52) U.S. Cl.
CPC ........ *A61M 39/223* (2013.01); *A61M 39/105* (2013.01); *A61M 2039/226* (2013.01)

(58) Field of Classification Search
CPC .............. A61M 39/105; A61M 39/223; A61M 39/26; A61M 2039/226; A61M 2039/262; A61M 2039/267; A61M 2039/268; A61M 39/1011; A61M 2039/1038
See application file for complete search history.

(56) References Cited

U.S. PATENT DOCUMENTS

| | | |
|---|---|---|
| 5,047,021 A | 9/1991 | Uttergerg |
| 5,766,211 A | 6/1998 | Wood et al. |
| 6,569,117 B1 * | 5/2003 | Ziv ........................ A61M 39/02 604/164.01 |
| 7,472,932 B2 | 1/2009 | Weber et al. |
| 8,353,859 B2 | 1/2013 | Derichs |
| D800,899 S | 10/2017 | Adams et al. |

FOREIGN PATENT DOCUMENTS

| | | |
|---|---|---|
| CN | 1148508 A | 4/1997 |
| CN | 1929799 B | 4/2011 |
| CN | 101277733 B | 7/2012 |
| CN | 107073245 A | 8/2017 |
| EP | 0869826 B1 | 10/2003 |
| JP | H09173470 A | 7/1997 |
| WO | 2008115439 A1 | 9/2008 |

* cited by examiner

*Primary Examiner* — Shefali D Patel
(74) *Attorney, Agent, or Firm* — Rothwell, Figg, Ernst & Manbeck, P.C.

(57) ABSTRACT

Systems and methods for directing fluid flow are described. In some embodiments, a system may include a first port, a second port, and a third port. The system may have a first state in which a male fitting of a device is not inserted in a female fitting of the third port. A valve assembly may block a first fluid path defined between the first port and the third port when the system is in the first state. The system may also have a second state in which the male fitting of the device is fully inserted in the female fitting of the third port. The valve assembly may block a second fluid path defined between the first port and the second port when the system is in the second state.

21 Claims, 9 Drawing Sheets

SYSTEMS AND METHODS FOR DIRECTING FLUID FLOW

FIELD OF THE DISCLOSURE

This disclosure relates to systems and methods for directing fluid flow. For example, this disclosure relates to systems and methods that may be used to control the direction of fluid flow, such that a channel may be selectively used to drain fluid or administer fluid to a portion of a patient's body.

BACKGROUND

A number of medical applications call for a single channel (e.g., a catheter) to carry fluid both to and from a bodily structure. As one example, urological procedures may use a catheter to drain fluid from a patient's bladder or kidney. Meanwhile, the same catheter may also be used to deliver compounds, such as cancer drugs, to the bladder or kidney. There is currently no adequate solution for effectively and efficiently controlling the direction of flow of a channel, so that a single channel may be easily used to carry fluid both to and from a bodily structure.

Accordingly, there is a need for systems and methods that can effectively and efficiently control the direction of flow of fluid through a channel. Further, there is a need for systems and methods that can automatically change the direction of flow when a device for inserting fluid, such as a syringe, is coupled to the channel.

SUMMARY

The following description presents a simplified summary in order to provide a basic understanding of some aspects described herein. This summary is not an extensive overview of the claimed subject matter. It is intended to neither identify key or critical elements of the claimed subject matter nor delineate the scope thereof.

In some embodiments, a system for directing fluid flow may be provided. The system may include a first port configured to be coupled to a first channel, a second port configured to be coupled to a second channel, and a third port configured to be coupled to a third channel. In some embodiments, the third port may include a female fitting. The system may further include a valve assembly and a central passage, which may connect the first port, the second port, and the third port. In some embodiments, the system may have a first state in which a male fitting of a device is not inserted in the female fitting of the third port. The valve assembly may block a first fluid path defined between the first port and the third port when the system is in the first state. The system may also have a second state in which a male fitting of a device is fully inserted in the female fitting of the third port. The valve assembly may block a second fluid path defined between the first port and the second port when the system is in the second state. In some embodiments, the system may be configured such that inserting a male fitting of a device into the female fitting of the third port causes the system to transition from the first state to the second state.

In some embodiments, a method for directing fluid flow may be provided. The method may be performed using a system including a first port, a second port, a third port, a central passage, and a valve assembly. The method may include connecting the first port to a first channel, connecting the second port a second channel, and connecting the third port to a third channel. In some embodiments, the third port may include a female fitting. The first port, the second port, and the third port may be connected to each other via the central passage. In some embodiments, the step of connecting the third port to the third channel may cause the system to transition from a first state to a second state. In the first state, the female fitting of the third port may be uncoupled to a male fitting of a device defining the third channel, and the valve assembly may block a first fluid path defined between the first port and the third port. In the second state, the male fitting of the device defining the third channel may be fully inserted in the female fitting of the third port, and the valve assembly may block a second fluid path defined between the first port and the second port.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Figure 1:
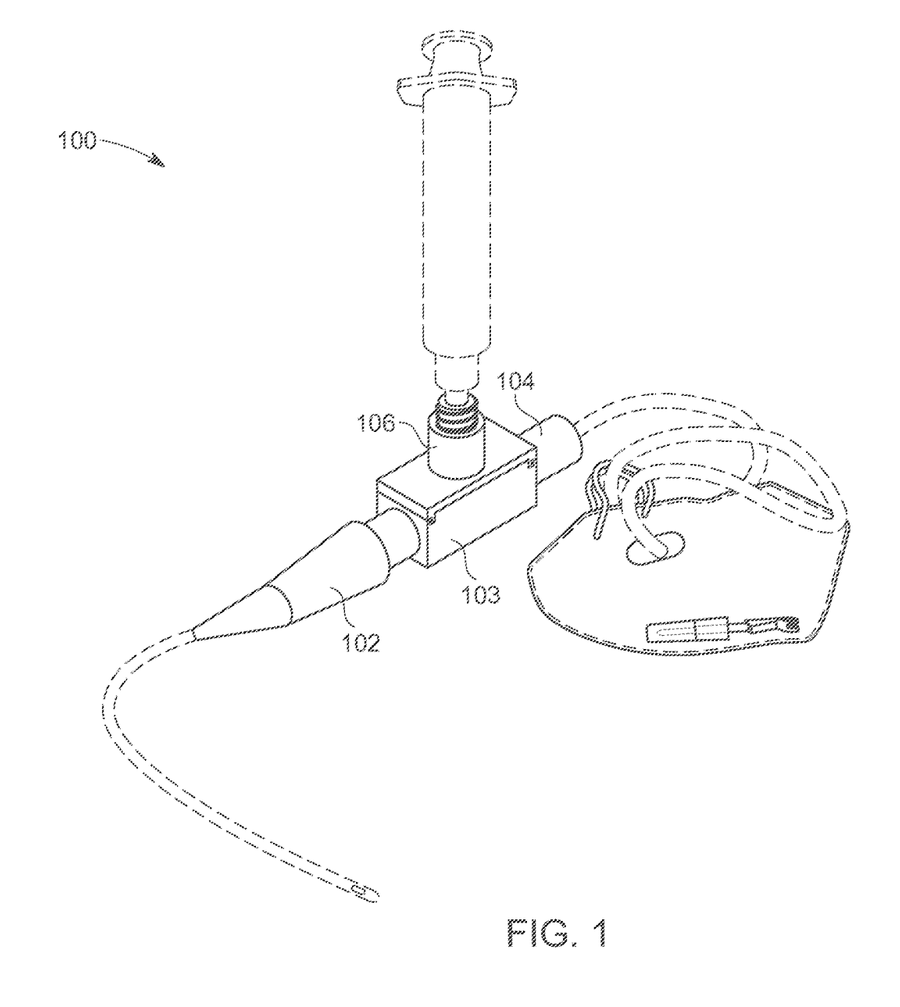
FIG. 1 shows an exemplary system for directing fluid flow.

FIG. 1 shows an exemplary system 100 for directing fluid flow. As used herein, the term 'fluid' may include both liquids and gases. The system 100 may include a first port 102, a second port 104, and a third port 106. The first port 102 may be configured to be coupled to a first channel. The second port 104 may be configured to be coupled to a second channel. The third port 106 may be configured to be coupled to a third channel. For example, in some embodiments, the first port 102 may be coupled to a channel, such as a catheter, that extends to a portion of a patient's body. The second port 104 may be coupled to a second channel, such as a drainage tube, which may receive fluid from the patient's body. The third port 106 may be coupled to a device, such as a syringe for administering fluid or taking samples or another fluid delivery device such as an IV bag with a connector, which may selectively administer or collect fluids. The system may include a body 103 disposed between the first port 102, second port 104, and third port 106.

Figure 2:
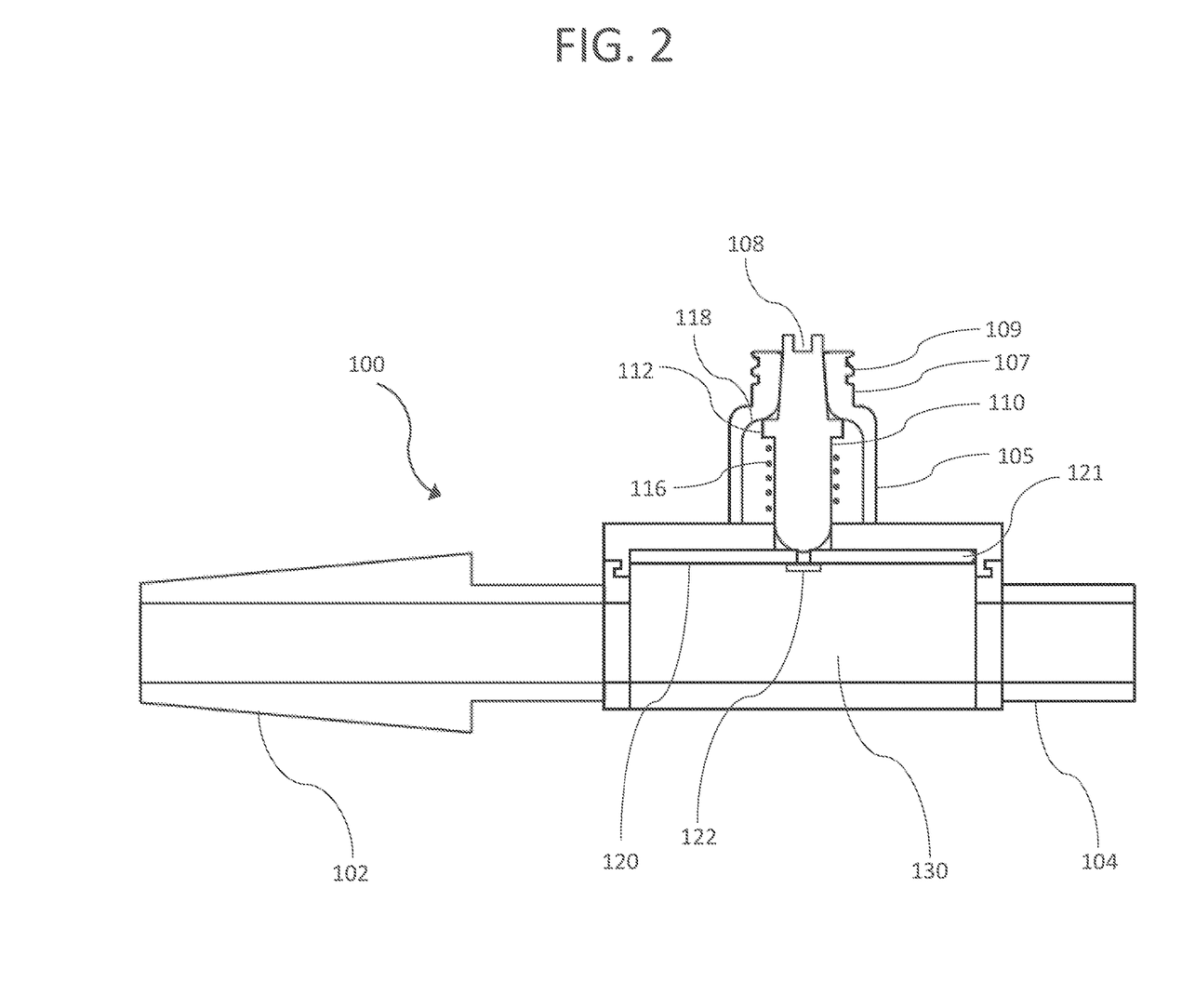
FIG. 2 shows a cross-sectional view of the system of FIG. 1 in a first state.

FIG. 2 shows a cross-sectional view of system 100. The system 100 may include a valve assembly, which may include one or more of a member 110 and a valve 120. The system may further include a central passage 130, which may connect the first port 102, second port 104, and third port 106 such that fluid may flow therebetween. The system 100 may define a first fluid path between the first port 102 and the third port 106. The system 100 may further define a second fluid path between the first port 102 and the second port 104. In some embodiments, the central passage 130 may have a length extending between the first port and the second port, and the central passage may have a cross-section in a plane that is normal to the length that is rectangular. In other embodiments, circular or oval cross-sections may be used. As used herein, terms relating to geometric shapes such as 'rectangular,' 'circular,' or 'oval' are intended to refer to approximations of these shapes with such deviations as may occur for purposes of manufacture.

As described herein, the system 100 may selectively transition between a first state (shown in FIG. 2) in which the valve assembly blocks the first fluid path defined between the first port 102 and the third port 106 and a second state (shown in FIG. 3) in which the valve assembly blocks the second fluid path defined between the first port 102 and the second port 104. In some embodiments, this transition may occur automatically when a male fitting of a device is inserted into a female fitting 108 of the third channel 106.

The third port 106 may include a female fitting 108, which may be sized and shaped to receive a male fitting of a device to which the third port 106 may be coupled. In some embodiments, the female fitting 108 may be a female fitting of a sealing taper (which may be, for example, a sealing taper). In some embodiments, the male fitting of the device may be a male fitting of a sealing taper. In some embodiments, the third port may include a thread 109. The thread 109 may be configured to engage a complementary thread on a device. For example, the female fitting 108 and thread 109 may together define a female portion of a Luer lock, which may be configured to engage a male portion of a Luer lock of a device.

The third port 106 may include a first portion 107 with a first diameter and a second portion 105 with a second diameter greater than the first diameter. In some embodiments, the first portion may have a diameter sized to engage a male fitting of a sealing taper. A shoulder 118 may be defined at a transition from the first portion 107 and the second portion 105.

The member 110 may include a flange 112 that may be configured to engage shoulder 118 when the system is in the first state. A spring 116 may be configured to bias the member 110 toward a position in which the flange 112 engages shoulder 118. For example, in some embodiments, the spring 116 may be disposed around a portion of the member 110 such that the spring 116 engages a surface of the flange 112 that is opposite the surface arranged to engage the shoulder 118. In other embodiments, a spring may be attached to pivot 121, which may bias valve 120 toward the position shown in FIG. 2 in which the system is in the first state. The valve 120, in turn, may press the member 110 into the position shown in FIG. 2.

Figure 3:
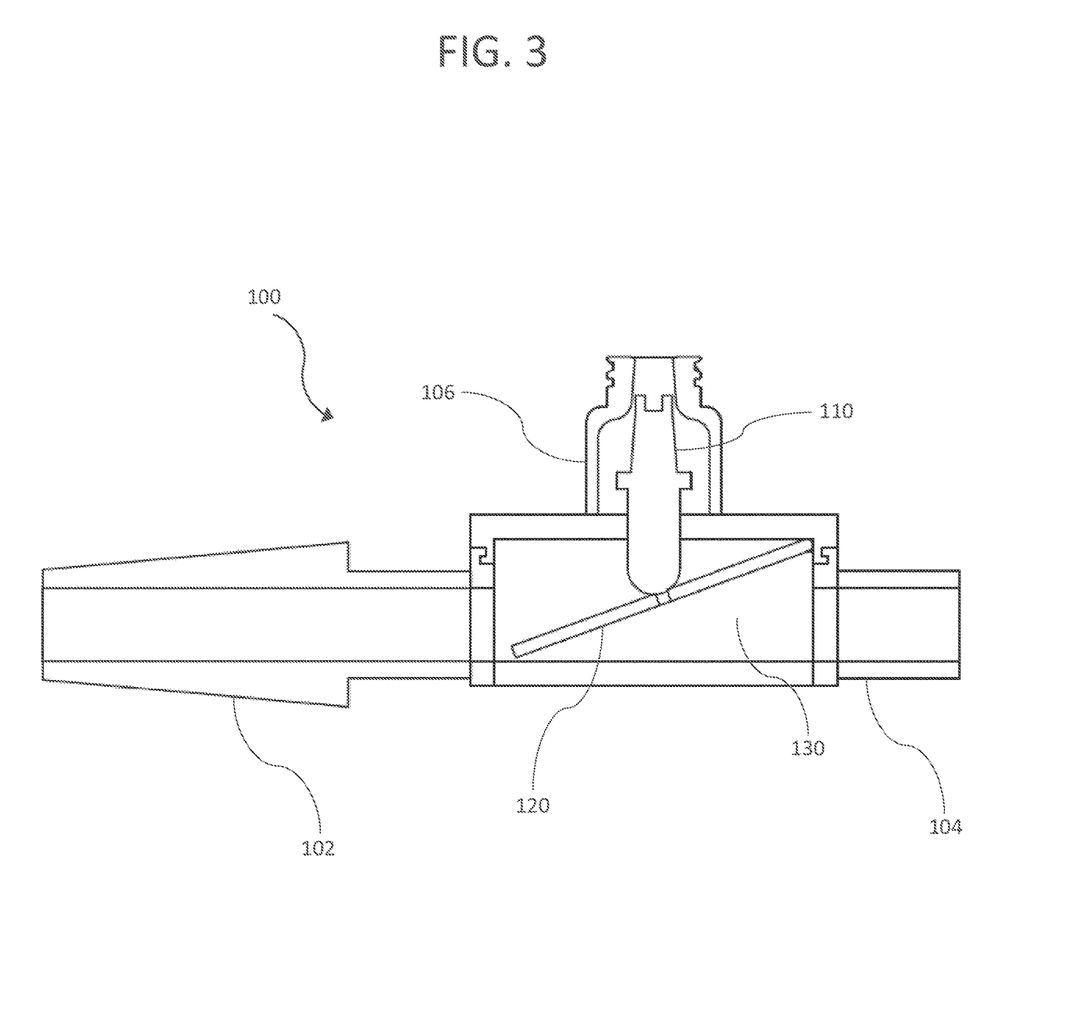
FIG. 3 shows a cross-sectional view of the system of FIG. 1 in a second state.

By inserting a male fitting of a device into the female fitting 108 of the third port 106, the system may be caused to transition to a second state, which is shown in FIG. 3. Specifically, the male fitting may press the member 110 downwardly (in the orientation shown in FIGS. 2 and 3) so that the member extends at least partially into or further into the central passage 130. This may cause the valve 120 to pivot such that it blocks the second fluid path between the first port 102 and the second port 104, and opens the first fluid path between the first port 102 and the second port 106. The dimensions and positions of the valve 120, body 103, and member 110 may be selected such that fully inserting a male fitting of a standardized size (e.g., a Luer taper) into the female fitting 108 automatically causes the valve to transition from its position in the first state to its position in the second state, thereby switching the system's open path from the second fluid path (between the first port 102 and the second port 104) to the first fluid path (between the first port 102 and the third port 106).

Removing the male fitting from the female fitting 108 may cause the system 100 to automatically transition from the second state to the first state. In some embodiments, the member 110 may be coupled to the valve 120. For example, a tether may extend from the member 110 through a hole in the valve (shown in FIG. 4) to an anchor 122. In this manner, the biasing force of spring 116 may cause the member 110 to return to the position shown in FIG. 2 when the male fitting of the device is removed from female fitting 108. This, in turn, may cause valve 120 to return to the position shown in FIG. 2 by operation of the tether and anchor 122. In other embodiments, the valve 120 may be biased to return to the position shown in FIG. 2 by a spring associated with pivot 121. In these embodiments, removing the male fitting from the female fitting 108 may allow the biasing force of the spring on pivot 121 to return the valve 120 to the position shown in FIG. 2, which may, in turn, push the member 110 to return to the position shown in FIG. 2.

In some embodiments, member 110 may have one or more openings defined therein. When a male fitting is inserted into the female fitting 108 of the third port 106 such that the male fitting engages the member 110, fluid may flow through the male fitting into a central channel defined by the member 110 and then out through openings. Alternatively, in an embodiment where the device having the male fitting is used to collect fluid (e.g., to collect a sample for analysis), fluid may flow in through openings, through the central channel defined by the member 110, and into the male fitting of the device.

Figure 4:
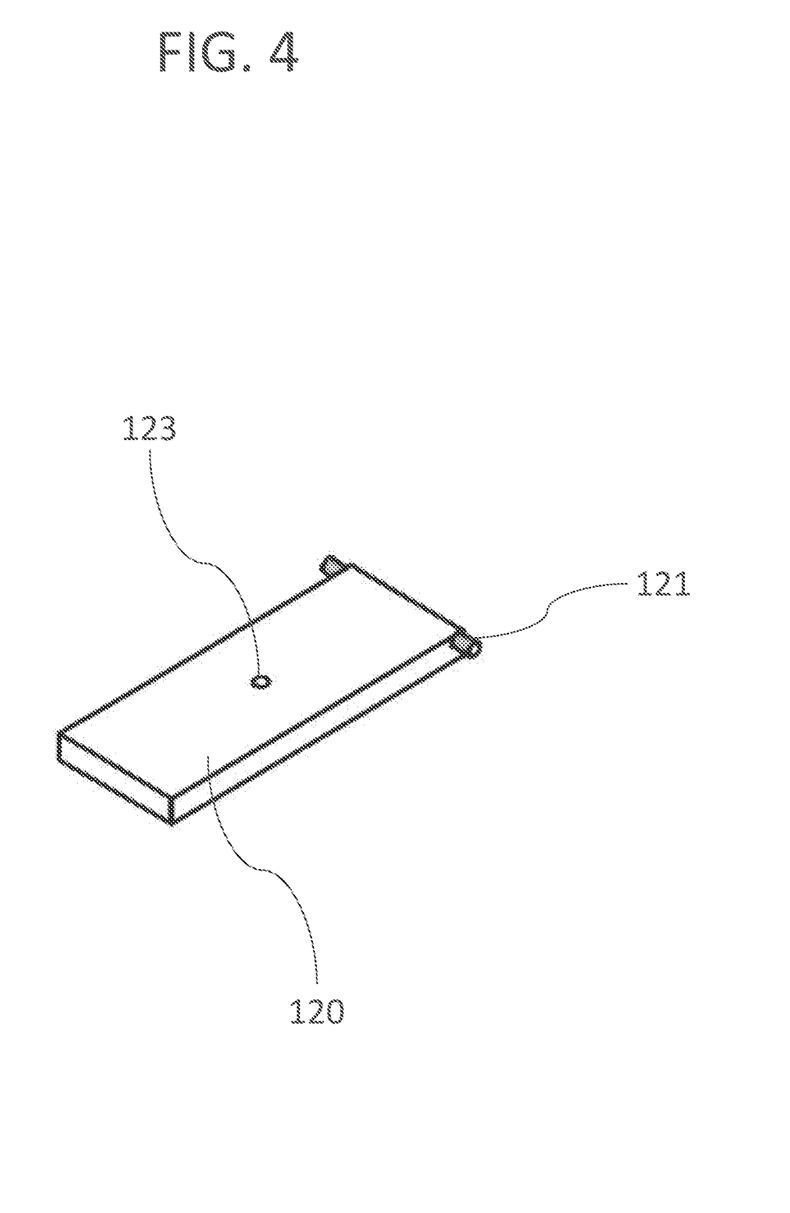
FIG. 4 shows an exemplary valve.

FIG. 4 shows an exemplary embodiment of a valve 120, which may be incorporated in a system such as that shown in FIGS. 1-3. The valve 120 may include a pivot 121, which may engage a complementary recess in the system 100, thereby allowing the valve to rotate about pivot 121. The valve may also include an opening 123, through which a tether may extend, as shown in FIG. 2.

Figure 5:
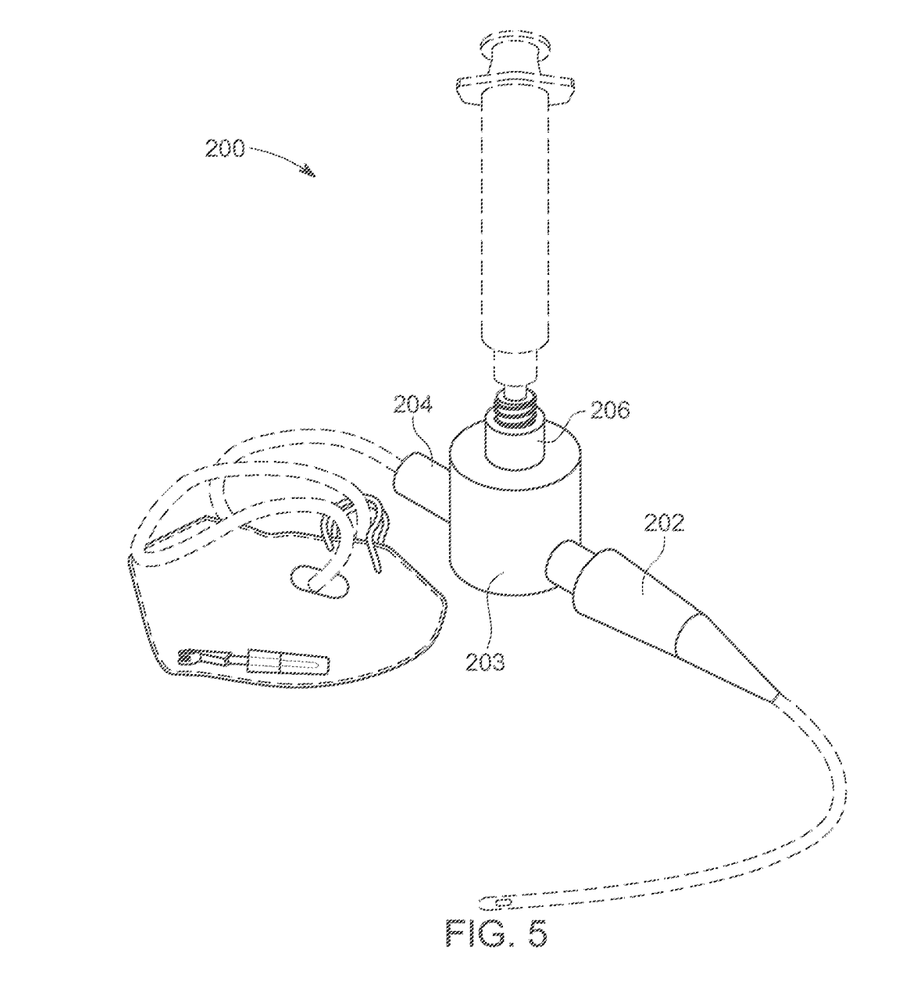
FIG. 5 shows another exemplary system for directing fluid flow.

FIG. 5 shows another exemplary system 200 for directing fluid flow. The system 200 may include a first port 202, a second port 204, and a third port 206. The first port 202 may be configured to be coupled to a first channel. The second port 204 may be configured to be coupled to a second channel. The third port 206 may be configured to be coupled to a third channel. For example, in some embodiments, the first port 202 may be coupled to a channel, such as a catheter, that extends to a portion of a patient's body. The second port 204 may be coupled to a second channel, such as a drainage tube, which may receive fluid from the patient's body. The third port 206 may be coupled to a device, such as a syringe for administering fluid or taking samples or another fluid delivery device such as an IV bag with a connector, which may selectively administer or collect fluids. The system may include a body 203 disposed between the first port 202, second port 204, and third port 206.

Figure 6:
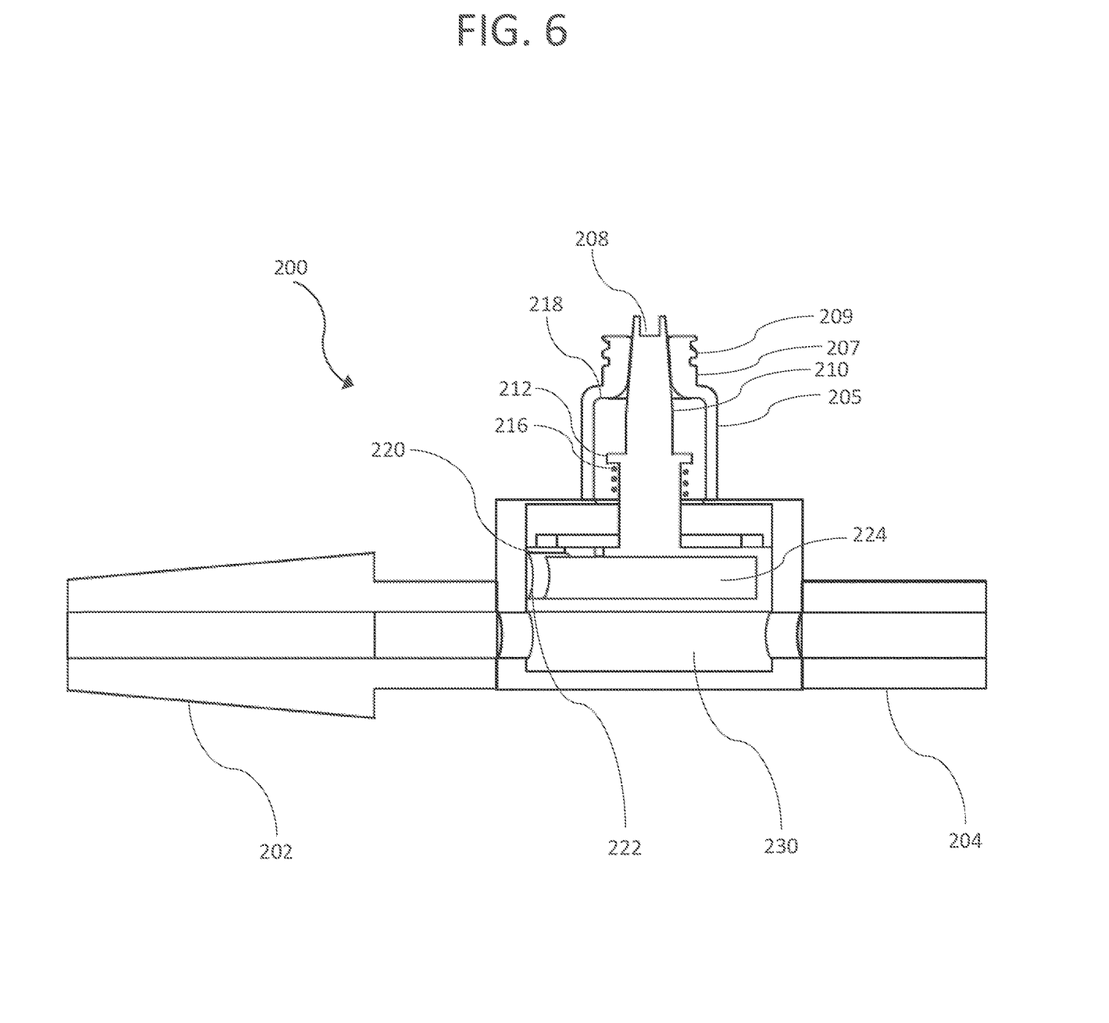
FIG. 6 shows a cross-sectional view of the system of FIG. 1 in a first state.

FIG. 6 shows a cross-sectional view of system 200. The system 200 may include a valve assembly, which may include a member 220. The member 220 may include a stem 210. The system may further include a central passage 230, which may connect the first port 202, second port 204, and third port 206 such that fluid may flow therebetween. The system 200 may define a first fluid path between the first port 202 and the third port 206. The system 200 may further define a second fluid path between the first port 202 and the second port 204. As described herein, the system 200 may selectively transition between a first state (shown in FIG. 6) in which the valve assembly blocks the first fluid path defined between the first port 202 and the third port 206 and a second state (shown in FIG. 7) in which the valve assembly blocks the second fluid path defined between the first port 202 and the second port 204. In some embodiments, this transition may occur automatically when a male fitting of a device is inserted into a female fitting 208 of the third channel 206.

The third port 206 may include a female fitting 208, which may be sized and shaped to receive a male fitting of a device to which the third port 206 may be coupled. In some embodiments, the female fitting 208 may be a female fitting of a sealing taper. In some embodiments, the male fitting of the device may be a male fitting of a sealing taper. In some embodiments, the third port may include a thread 209. The thread 209 may be configured to engage a complementary thread on a device. For example, the female fitting 208 and thread 209 may together define a female portion of a sealing lock, which may be configured to engage a male portion of a Luer lock of a device.

The third port 206 may include a first portion 207 with a first diameter and a second portion 205 with a second diameter greater than the first diameter. In some embodiments, the first portion may have a diameter sized to engage a male fitting of a sealing taper. A shoulder 218 may be defined at a transition from the first portion 207 and the second portion 205.

The member 220 may include a flange 212 that may be configured to engage shoulder 218 when the system is in the first state. A spring 216 may be configured to bias the member 220 toward a position in which the flange 212 engages shoulder 218. For example, in some embodiments, the spring 216 may be disposed around a portion of the member 220 such that the spring 216 engages a surface of the flange 212 that is opposite the surface arranged to engage the shoulder 218.

Figure 7:
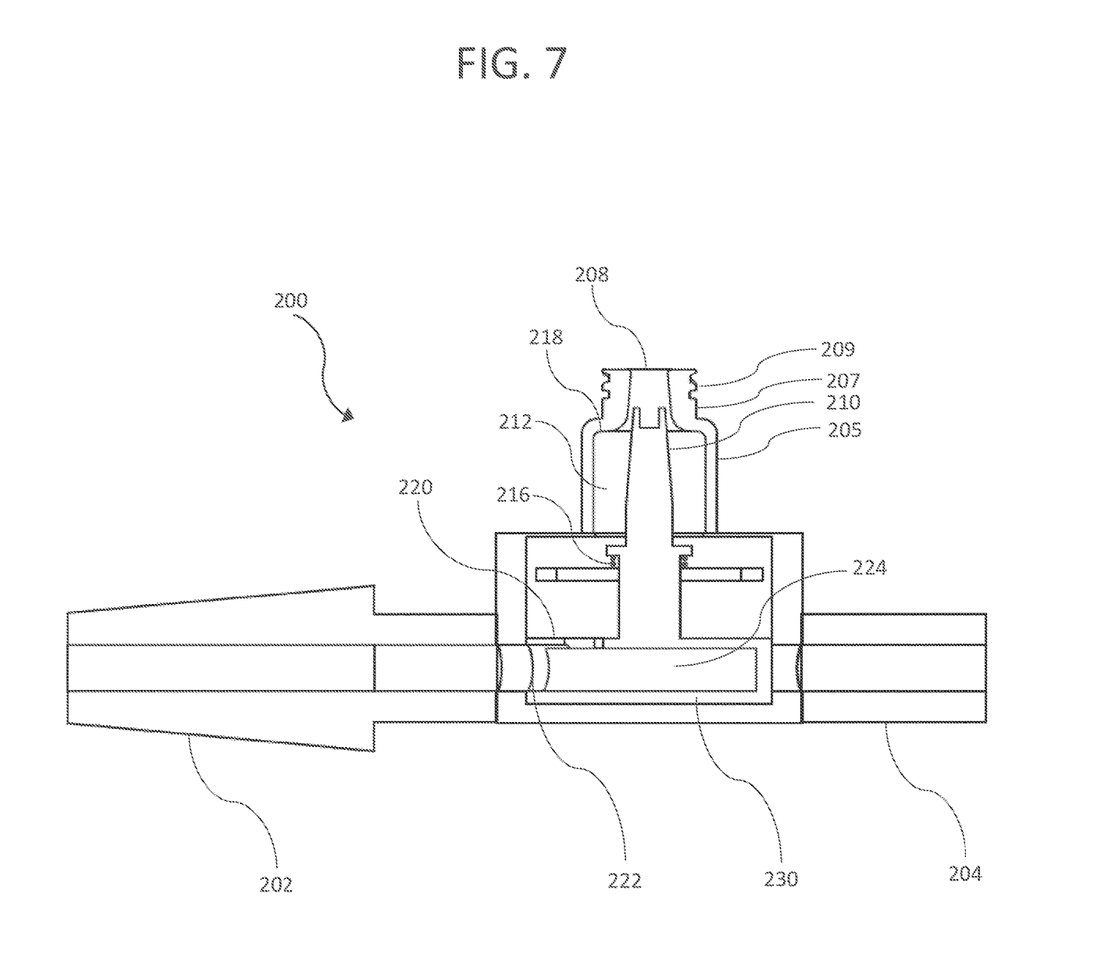
FIG. 7 shows a cross-sectional view of the system of FIG. 1 in a second state.

By inserting a male fitting of a device into the female fitting 208 of the third port 206, the system may be caused to transition to a second state, which is shown in FIG. 7. Specifically, the male fitting may press the member 220 downwardly (in the orientation shown in FIGS. 6 and 7) so that the member extends at least partially into or further into the central passage 230. This may cause the member 220 to block the second flow path between the first port 202 and the second port 204. It may also cause an opening 222 to align with a passage through the first port 202 such that fluid may flow between the first port 202 and a channel 224 defined within the member 220. To ensure alignment, the member 220 and body 203 may include complementary grooves, fittings, or other alignment arrangements, that may run vertically and ensure that opening 222 aligns properly with the channel of port 202 when the system 200 is in the second state (shown in FIG. 7). In some embodiments, a releasable locking member may be provided to releasably maintain the system in the second state in the event that the male fitting of the device is inadvertently detached from the female fitting 208 of the second port. So arranged, the system may transition from the second state to the first state when the male fitting is removed and the locking mechanism is released. The member 220 may be arranged such that when the system 200 is in the second state, fluid may flow from the first port 202, into the first opening 222 of the member 220, through the channel 224 of the member 220, out of a second opening 228 (see FIG. 8) of the member 220, and out of the third port 206. Fluid may likewise flow through the same components in the opposite direction.

The dimensions and positions of the member 220 and body 203 may be selected such that fully inserting a male fitting of a standardized size (e.g., a Luer taper) into the female fitting 208 automatically causes the valve assembly to transition from its position in the first state to its position in the second state, thereby switching the system's open path from the second fluid path (between the first port 202 and the second port 204) to the first fluid path (between the first port 202 and the third port 206).

Removing the male fitting from the female fitting 208 may cause the system 200 to automatically transition from the second state to the first state. For example, the biasing force of spring 216 may cause the member 220 to return to the position shown in FIG. 6 when the male fitting of the device is removed from female fitting 208.

Figure 8:
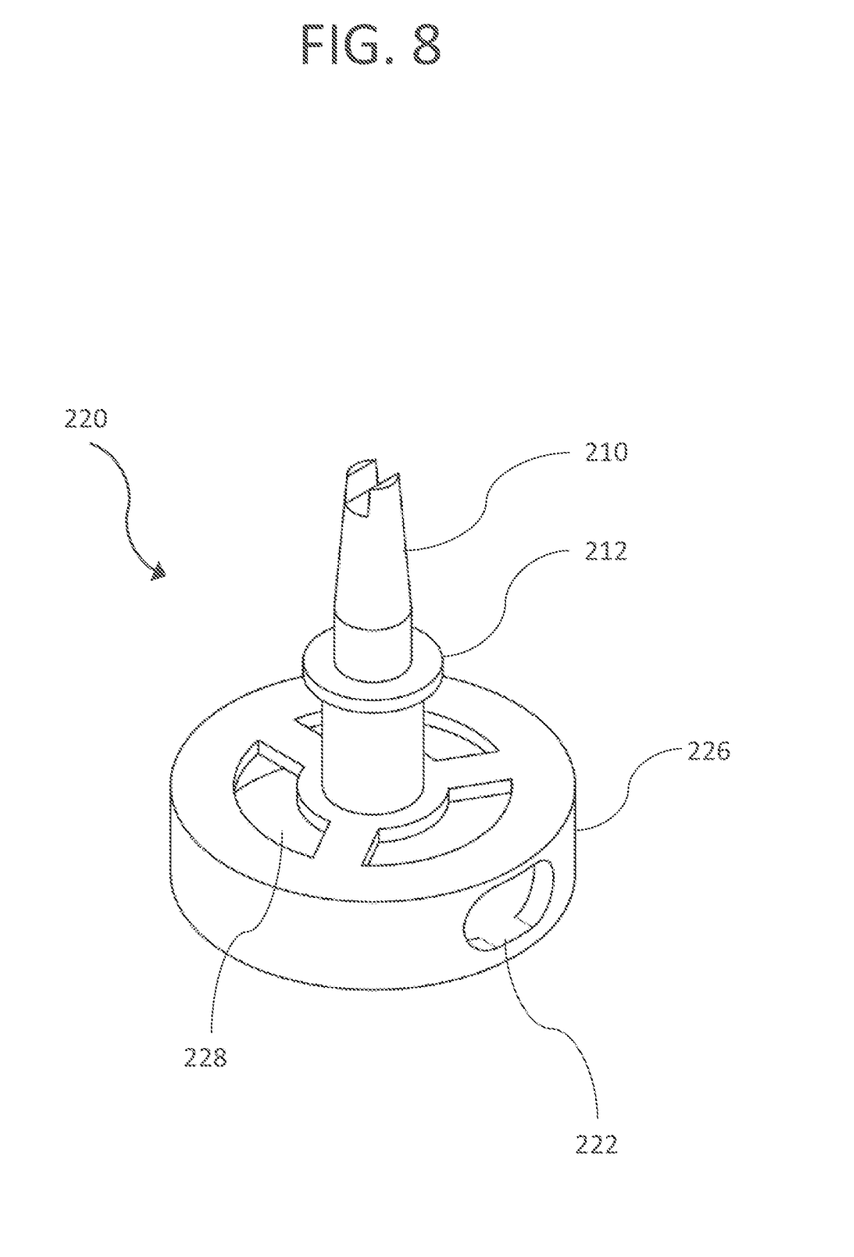
FIG. 8 shows an exemplary member which may be part of a valve assembly.

FIG. 8 shows an exemplary embodiment of a member 220, which may be incorporated in a system such as that shown in FIGS. 5-7. The member 220 may include a stem 210 and a body 226. The stem 210 may include a flange 212, as described above. An opening 222 may connect to a channel 224 defined within the member 220 (see FIG. 6). The member 220 may also include one or more openings 228, which may allow fluid to flow into or out the channel 224. In this manner, fluid at one end of the member 220 may flow through the channel 224, provided that the openings 222, 228 are not blocked. When the system 200 is in the first state (shown in FIG. 6) opening 222 may be blocked by a wall of body 203. When the system 200 is in the second state (shown in FIG. 7), opening 222 may align with a port channel fluid may flow through channel 224 and openings 222, 228.

Figure 9:
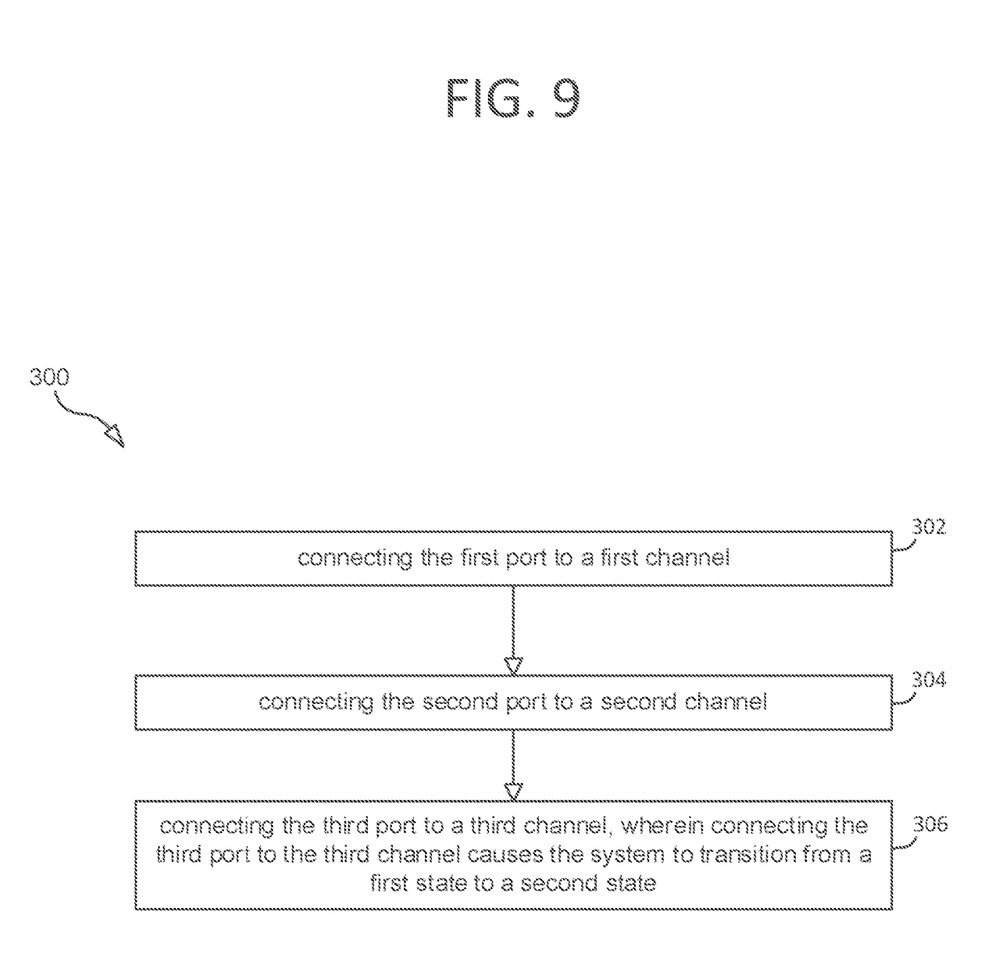
FIG. 9 shows an exemplary method for directing fluid flow.

FIG. 9 shows an exemplary method 300 for directing fluid flow. In some embodiments, method 300 may be performed method being performed using a system such as system 100 or system 200, as described above with respect to FIGS. 1-8. For example, method 300 may be performed using a system that includes a first port, a second port, a third port, a central passage, and a valve assembly. In some embodiments, the third port may include a female fitting. The first port, the second port, and the third port may be connected to each other via the central passage. In step 302, the first port may be connected to a first channel. In step 304, the second port may be connected to a third channel. In step 306, the third port may be connected to a third channel. In some embodiments, the step of connecting the third port to the third channel may cause the system to transition from a first state to a second state, as described above with respect to FIGS. 1-8. For example, in the first state, a male fitting of a device defining the third channel may be not inserted in the female fitting of the third port, and the valve assembly may block a first fluid path defined between the first port and the third port. In the second state, the male fitting of the device defining the third channel may be fully inserted in the female fitting of the third port, and the valve assembly may block a second fluid path defined between the first port and the second port.

In some embodiments, the male fitting of the device defining the third channel is a male fitting of a Luer taper. For example, the device defining the third channel may be a syringe having a male fitting of a Luer taper, such that the syringe may easily connect to devices with corresponding female fittings.

In some embodiments, the valve assembly may include a member that is at least partially disposed in the third port when the system is in the first state, and the step 306 of connecting the third port to the third channel may include inserting the male fitting of the device into the female fitting of the third port, thereby causing the member to extend at least partially into or further into the passage (as described above with respect to FIGS. 1-8). In some embodiments, the system may be in the first state before the step 306 of connecting the third port to the third channel. In this state, a spring may bias the member such that the member is at least partially disposed in the third port. In some embodiments, the third port may include a first portion having a first diameter sized to engage a male fitting of a sealing taper such as Luer lock, and a second portion having a second diameter that is greater than the first diameter.

In some embodiments, the member may include one or more flanges. When the system is in the first state, a first surface of the one or more flanges may engage a shoulder of the third port, and a second surface of the one or more flanges may engage a spring. For example, a spring may be arranged generally as springs 116, 216 are shown in FIGS. 2 and 6. The spring may bias the member such that the member is at least partially disposed in the third port when the system is in the first state.

In some embodiments, the valve assembly may include a leaf, as described above with respect to FIGS. 1-4. The leaf may be biased toward a first position in which the leaf blocks the first fluid path defined between the first port and the third port when the system is in the first state. In some embodiments, the step 306 of connecting the third port to the third channel, thereby transitioning the system from the first state to the second state, may cause the member to contact the leaf and press it into a second position in which the leaf blocks the second fluid path defined between the first port and the second port when the system is in the second state.

In some embodiments, the step 306 of connecting the third port to the third channel, thereby transitioning the system from the first state to the second state, may cause the member to block the second fluid path defined between the first port and the second port, as described above with respect to FIGS. 5-8. In some embodiments, the member may include a channel, a first opening, and a second opening. For example, the openings may be arranged generally as shown in FIG. 8, though many other arrangements for the openings are acceptable. The system may be configured such that when the system is in the second state, fluid may flow from the first port, into the first opening of the member, through the channel of the member, out of the second opening of the member, and out of the third port.

NUMBERED EMBODIMENTS

Certain exemplary embodiments are enumerated below.

A1. A system for directing fluid flow, the system comprising:
a first port configured to be coupled to a first channel;
a second port configured to be coupled to a second channel;
a third port configured to be coupled to a third channel, the third port comprising a female fitting;
a central passage, the central passage connecting the first port, the second port, and the third port; and
a valve assembly;
wherein:
the system has a first state in which a male fitting of a device is not inserted in the female fitting of the third port, the valve assembly blocking a first fluid path defined between the first port and the third port when the system is in the first state;
the system has a second state in which a male fitting of a device is fully inserted in the female fitting of the third port, the valve assembly blocking a second fluid path defined between the first port and the second port when the system is in the second state; and
the system is configured such that inserting a male fitting of a device into the female fitting of the third port causes the system to transition from the first state to the second state.

A2. The system of embodiment A1, wherein the system further comprises:
a first channel coupled to the first port;
a second channel coupled to the second port; and
a device defining a third channel, the device comprising a male fitting that is inserted in the female fitting of the third port.

A3. The system of any of embodiments A1-A2, wherein the central passage has a length extending between the first port and the second port, the central passage having a cross-section in a plane that is normal to the length, the cross-section being rectangular.

A4. The system of any of embodiments A1-A4, further wherein:
the valve assembly comprises a member that is at least partially disposed in the third port when the system is in the first state; and
the system is arranged such that inserting a male fitting of a device into the female fitting of the third port causes the member to extend at least partially into or further into the passage.

A5. The system of embodiment A4, further comprising a spring that biases the member toward a position in which the member is at least partially disposed in the third port when the system is in the first state.

A6. The system of any of embodiments A4-A5, wherein the third port comprises:
a first portion having a first diameter sized to engage a male fitting of a sealing taper; and
a second portion having a second diameter that is greater than the first diameter.

A7. The system of embodiment A6, further wherein:
the member comprises one or more flanges;
when the system is in the first state, a first surface of the one or more flanges engages a shoulder of the third port; and
a second surface of the one or more flanges engages a spring, the spring biasing the member such that the member is at least partially disposed in the third port when the system is in the first state.

A8. The system of any of embodiments A4-A7, further wherein:
the valve assembly comprises a leaf, the leaf being biased toward a first position in which the leaf blocks the first fluid path defined between the first port and the third port when the system is in the first state; and
the system is configured such that when the system is in the second state, the member contacts the leaf and presses it into a second position in which the leaf blocks the second fluid path defined between the first port and the second port when the system is in the second state.

A9. The system of any of embodiments A4-A7, further wherein:

the member is configured to block the second fluid path defined between the first port and the second port when the system is in the second state.

A10. The system of embodiment A9, further wherein:

the member comprises a channel, a first opening, and a second opening; and the system is configured such that when the system is in the second state, fluid may flow from the first port, into the first opening of the member, through the channel of the member, out of the second opening of the member, and out of the third port.

A11. The system of any of embodiments A1-A10, wherein the female fitting of the third port is sized to receive a male fitting of sealing taper.

B1. A method for directing fluid flow, the method being performed using a system comprising a first port, a second port, a third port, a central passage, and a valve assembly, the method comprising:

connecting the first port to a first channel;
connecting the second port a second channel; and
connecting the third port to a third channel, the third port comprising a female fitting, wherein the first port, the second port, and the third port are connected to each other via the central passage;

wherein:
the step of connecting the third port to the third channel causes the system to transition from a first state to a second state;
in the first state, a male fitting of a device defining the third channel is not is inserted in the female fitting of the third port, and the valve assembly blocks a first fluid path defined between the first port and the third port; and
in the second state, the male fitting of the device defining the third channel is fully inserted in the female fitting of the third port, and the valve assembly blocks a second fluid path defined between the first port and the second port.

B2. The method of embodiment B1, wherein the male fitting of the device defining the third channel is a male fitting of a sealing taper.

B3. The method of any of embodiments B1-B2, wherein the central passage has a length extending between the first port and the second port, the central passage having a cross-section in a plane that is normal to the length, the cross-section being rectangular.

B4. The method of any of embodiments B1-B3, further wherein:

the valve assembly comprises a member that is at least partially disposed in the third port when the system is in the first state; and the step of connecting the third port to the third channel comprises inserting the male fitting of the device into the female fitting of the third port, thereby causing the member to extend at least partially into or further into the passage.

B5. The method of embodiment B4, wherein, prior to connecting the third port to the third channel, the system is in the first state and a spring biases the member such that the member is at least partially disposed in the third port.

B6. The method of any of embodiments B4-B5, wherein the third port comprises:

a first portion having a first diameter sized to engage a male fitting of a sealing taper; and a second portion having a second diameter that is greater than the first diameter.

B7. The method of embodiment B6, further wherein:

the member comprises one or more flanges;
when the system is in the first state, a first surface of the one or more flanges engages a shoulder of the third port; and
a second surface of the one or more flanges engages a spring, the spring biasing the member such that the member is at least partially disposed in the third port when the system is in the first state.

B8. The method of any of embodiments B4-B7, further wherein:

the valve assembly comprises a leaf, the leaf being biased toward a first position in which the leaf blocks the first fluid path defined between the first port and the third port when the system is in the first state; and the step of connecting the third port to the third channel, thereby transitioning the system from the first state to the second state, causes the member to contact the leaf and press it into a second position in which the leaf blocks the second fluid path defined between the first port and the second port when the system is in the second state.

B9. The method of any of embodiments B4-B7, further wherein:

the step of connecting the third port to the third channel, thereby transitioning the system from the first state to the second state, causes the member to block the second fluid path defined between the first port and the second port.

B10. The method of embodiment B9, further wherein:

the member comprises a channel, a first opening, and a second opening; and the system is configured such that when the system is in the second state, fluid may flow from the first port, into the first opening of the member, through the channel of the member, out of the second opening of the member, and out of the third port.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A system for directing fluid flow, the system comprising:

a first port configured to be coupled to a first channel;
a second port configured to be coupled to a second channel;
a third port configured to be coupled to a device defining a third channel, the third port comprising a female fitting with an internal surface and an external surface, the external surface of the female fitting comprising a thread configured to engage a Luer lock;
a stem, the stem being disposed at least partially within the third port;
a central passage, the central passage connecting the first port, the second port, and the third port; and
a valve assembly;
wherein:

the system has a first state in which a male fitting of the device is not inserted in the female fitting of the third port, the valve assembly blocking a first fluid path defined between the first port and the third port when the system is in the first state, and a top of the stem extending beyond the third port in a direction away from the central passage when the system is in the first state;

the system has a second state in which the male fitting of the device is fully inserted in the female fitting of the third port, the valve assembly blocking a second fluid path defined between the first port and the second port when the system is in the second state, and the top of the stem being below the thread that is configured to engage the Luer lock in a direction toward the central passage when the system is in the second state; and the system is configured such that inserting the male fitting of the device into the female fitting of the third port causes the system to transition from the first state to the second state.

2. The system of claim 1, wherein the system further comprises:
the first channel coupled to the first port;
the second channel coupled to the second port; and
the device defining the third channel, the device comprising the male fitting that is inserted in the female fitting of the third port.

3. The system of claim 1, wherein the central passage has a length extending between the first port and the second port, the central passage having a cross-section in a plane that is normal to the length, the cross-section being rectangular.

4. The system of claim 1, further comprising a spring that biases the stem toward a position in which the stem is at least partially disposed in the third port when the system is in the first state.

5. The system of claim 1, wherein the third port comprises:
a first portion having a first diameter sized to a sealing taper of the male fitting of the device; and
a second portion having a second diameter that is greater than the first diameter.

6. The system of claim 5, further wherein:
the stem is coupled to one or more flanges;
when the system is in the first state, a first surface of the one or more flanges engages a shoulder of the third port; and
a second surface of the one or more flanges engages a spring, the spring biasing the stem such that the stem is at least partially disposed in the third port when the system is in the first state.

7. The system of claim 1, further wherein:
the valve assembly comprises a leaf, the leaf being biased toward a first position in which the leaf blocks the first fluid path defined between the first port and the third port when the system is in the first state; and
the system is configured such that when the system is in the second state, the stem contacts the leaf and presses the leaf into a second position in which the leaf blocks the second fluid path defined between the first port and the second port when the system is in the second state.

8. The system of claim 1, further wherein:
the stem is coupled to a member that is configured to block the second fluid path defined between the first port and the second port when the system is in the second state.

9. The system of claim 8, further wherein:
the member comprises a channel, a first opening, and a second opening; and
the system is configured such that when the system is in the second state, fluid may flow from the first port, into the first opening of the member, through the channel of the member, out of the second opening of the member, and out of the third port.

10. The system of claim 8, wherein:
the member has a lower surface in a direction opposite the third port, the lower surface of the member defining a lower boundary of the member;
the central passage has a lower internal surface that defines a lower boundary of the central passage;
when the system is in the first state, the lower surface of the member is out of contact with the lower internal surface of the central passage; and
when the system is in the second state, the lower surface of the member is in contact with the lower internal surface of the central passage.

11. The system of claim 1, wherein the female fitting of the third port is sized to receive a sealing taper of the male fitting of the device.

12. A method for directing fluid flow, the method being performed using a system comprising a first port, a second port, a third port, a stem disposed at least partially within the third port, a central passage, and a valve assembly, the method comprising:
connecting the first port to a first channel;
connecting the second port to a second channel; and
connecting the third port to a third channel, the third port comprising a female fitting having an internal surface and an external surface that comprises a thread configured to engage a Luer lock, wherein the first port, the second port, and the third port are connected to each other via the central passage;
wherein:
the step of connecting the third port to the third channel causes the system to transition from a first state to a second state;
in the first state, a male fitting of a device defining the third channel is not inserted in the female fitting of the third port, a top of the stem extends beyond the third port in a direction away from the central passage, and the valve assembly blocks a first fluid path defined between the first port and the third port; and
in the second state, the male fitting of the device defining the third channel is fully inserted in the female fitting of the third port, the top of the stem is below the thread that is configured to engage the Luer lock in a direction toward the central passage, and the valve assembly blocks a second fluid path defined between the first port and the second port.

13. The method of claim 12, wherein the male fitting of the device defining the third channel is a male fitting of a sealing taper.

14. The method of claim 12, wherein the central passage has a length extending between the first port and the second port, the central passage having a cross-section in a plane that is normal to the length, the cross-section being rectangular.

15. The method of claim 12, wherein, prior to connecting the third port to the third channel, the system is in the first state and a spring biases the stem such that the stem is at least partially disposed in the third port.

16. The method of claim 12, wherein the third port comprises:
- a first portion having a first diameter sized to engage a sealing taper of the male fitting of the device; and
- a second portion having a second diameter that is greater than the first diameter.

17. The method of claim 16, further wherein:
the stem is coupled to one or more flanges;
when the system is in the first state, a first surface of the one or more flanges engages a shoulder of the third port; and
a second surface of the one or more flanges engages a spring, the spring biasing the stem such that the stem is at least partially disposed in the third port when the system is in the first state.

18. The method of claim 12, farther wherein:
the valve assembly comprises a leaf, the leaf being biased toward a first position in which the leaf blocks the first fluid path defined between the first port and the third port when the system is in the first state; and
the step of connecting the third port to the third channel, thereby transitioning the system from the first state to the second state, causes the stem to contact the leaf and press the leaf into a second position in which the leaf blocks the second fluid path defined between the first port and the second port when the system is in the second state.

19. The method of claim 12, farther wherein:
the step of connecting the third port to the third channel, thereby transitioning the system from the first state to the second state, causes a member coupled to the stem to block the second fluid path defined between the first port and the second port.

20. The method of claim 19, further wherein:
the member comprises a channel, a first opening, and a second opening; and
the system is configured such that when the system is in the second state, fluid may flow from the first port, into the first opening of the member, through the channel of the member, out of the second opening of the member, and out of the third port.

21. The method of claim 19, wherein:
the member has a lower surface in a direction opposite the third port, the lower surface of the member defining a lower boundary of the member;
the central passage has a lower internal surface that defines a lower boundary of the central passage;
when the system is in the first state, the lower surface of the member is out of contact with the lower internal surface of the central passage; and
when the system is in the second state, the lower surface of the member is in contact with the lower internal surface of the central passage.

* * * * *